US009073848B2

(12) United States Patent
Jongmans et al.

(10) Patent No.: US 9,073,848 B2
(45) Date of Patent: Jul. 7, 2015

(54) PROCESS FOR SEPARATING MONOCHLOROACETIC ACID AND DICHLOROACETIC ACID VIA EXTRACTIVE DISTILLATION

(75) Inventors: Mark Theodorus Gerardus Jongmans, Deventer (NL); Johannes Josef Pragt, Dieren (NL); Gerrald Bargeman, Wageningen (NL); Boelo Schuur, Eindhoven (NL); Jacobus Theodorus Josef Aaldering, Doesburg (NL); André Banier De Haan, Eindhoven (NL); Melle Rinze Nieuwhof, Dieren (NL); Paul Verwer, Nijmegen (NL); Anton Alexandru Kiss, Arnhem (NL); Antoon Jacob Berend Ten Kate, Arnhem (NL); Cornelis Johannes Govardus Van Strien, Elst (NL)

(73) Assignee: AKZO NOBEL CHEMICALS INTERNATIONAL B.V., Amersfoort (NL)

(*) Notice: Subject to any disclaimer, the term of this patent is extended or adjusted under 35 U.S.C. 154(b) by 0 days.

(21) Appl. No.: 14/126,270

(22) PCT Filed: Mar. 13, 2012

(86) PCT No.: PCT/EP2012/054310
§ 371 (c)(1),
(2), (4) Date: Dec. 13, 2013

(87) PCT Pub. No.: WO2012/175229
PCT Pub. Date: Dec. 27, 2012

(65) Prior Publication Data
US 2014/0121411 A1    May 1, 2014

Related U.S. Application Data

(60) Provisional application No. 61/504,422, filed on Jul. 5, 2011.

(30) Foreign Application Priority Data

Jun. 21, 2011    (EP) .................................... 11170773

(51) Int. Cl.
| C07C 51/50 | (2006.01) |
| C07C 51/44 | (2006.01) |
| C07C 51/48 | (2006.01) |
| C07C 51/62 | (2006.01) |
| C07C 51/46 | (2006.01) |

(52) U.S. Cl.
CPC ................. *C07C 51/50* (2013.01); *C07C 51/44* (2013.01); *C07C 51/48* (2013.01); *C07C 51/62* (2013.01); *C07C 51/46* (2013.01)

(58) Field of Classification Search
CPC combination set(s) only.
See application file for complete search history.

(56) References Cited

U.S. PATENT DOCUMENTS

| 1,921,717 A | * | 8/1933 | Amstutz | ........................ 562/603 |
| 3,772,157 A | * | 11/1973 | Horsley | .......................... 203/52 |

FOREIGN PATENT DOCUMENTS

| JP | 4729886 | * | 1/1972 |
| JP | 4730165 | * | 1/1972 |

OTHER PUBLICATIONS

David R. Lide ed., CRC Handbook of Chemistry and Physics, 72nd Edition, pp. 3-17, 3-18, 3-20, and 3-427, CRC Press, Inc.,1991.
Stanley H. Pine, Organic Chemistry, Fifth Edition, pp. 98-118, McGraw-Hill Book Company, International Edition 1987.
Dejanovic et al., "Dividing Wall Column—A breakthrough towards sustainable distilling", Chemical Engineering and Processing, 2010, vol. 49, pp. 559-580.
Duprat et al., "Reactive Distillation of Pyridine Mixtures with an Organic Acid., I. Determination of the Reactive Distillation Equilibrium", Canadian Journal of Chemical Engineering, Dec. 1991, vol. 69, pp. 1320-1326.
Gaikar et al., "Extractive Distillation of p-Cresol/2,6-Xylenol Mixtures in the Presence of Alkanolamines", Separation Science and Technology, 1996, 31(14), pp. 1979-1988.
Gaikar et al., "New strategies for separations through reactions", Sadhana, Apr. 1987, vol. 10, parts 1 & 2, pp. 163-183.
Jagirdar et al., "Recovery and separation of mixtures of organic acids from dilute aqueous solutions", J. Separ. Proc. Technol., 1980, 1 (2), pp. 40-43.
Lei et al., "Separation of acetic acid and water by complex extractive distillation", Separation and Purification Technology, 2004, vol. 36, pp. 131-138.
Zhigang et al., "Separation of aqueous isopropanol by reactive extractive distillation", Journal of Chemical Technology and Biotechnology, online 2002, vol. 77, pp. 1251-1254.
Ningoo et al., "Extractive distillation of m/p-cresols mixtures in presence of reactive entrainers", Sep. Technol. Oct. 1994, vol. 4, pp. 249-251.

(Continued)

Primary Examiner — Karl J Puttlitz
(74) Attorney, Agent, or Firm — Kenyon & Kenyon LLP

(57) ABSTRACT

The present invention pertains to a process for separating monochloroacetic acid and dichloroacetic acid from one another via extractive distillation, comprising the steps of (i) contacting a mixture comprising monochloroacetic acid and dichloroacetic acid with an extractive agent which is chemically stable and which has a $BF_3$ affinity of between 65 kJ/mole and 110 kJ/mole, (ii) distilling the mixture to obtain a monochloroacetic acid stream and a stream comprising dichloroacetic acid and the extractive agent, and (iii) regenerating the extractive agent.

20 Claims, No Drawings

(56) References Cited

OTHER PUBLICATIONS

Richardson et al., "Particle Technology & Separation Processes", Coulson & Richardson's Chermical Engineering, 2002, vol. 2, fifth edition, pp. 616-628.

Terrill et al. "Separation of Closely Boiling Mixtures by Reactive Distillation—1. Theory", Ind. Eng. Chem. Process Des. Dev. 1985, vol. 24, pp. 1062-1071.

Laurence et al., "The BF3 Affinity Scale" (Chapter 3), "The Measurement of Lewis Basicity and Affinity in the Laboratory" (Chapter 7), Lewis Basicity and Affinity Scales, Data and Measurement, 2010, John Wiley & Sons Ltd. ISBN 978-0-470-74957-9, Chapters 3 and 7.

International Search Report and The Written Opinion of the International Searching Authority for International Application No. PCT/EP2012/054310, mailed on May 3, 2012.

Database WPI Week 197233, Thomson Scientific, London, GB; AN 1972-51786T, XP002663904, 1972.

Freund et al., "Process Intensification, 4. Plant Level", published Online: Jul. 15, 2011, p. 22 in Ullman's Encyclopedia of Industrial Chemistry: Extractive Distillation (187-190).

European Search Report for Application 11170773.3-1211, mailed on Nov. 28, 2011.

Richardson et al., "Particle Technology & Separation Processes", Coulson & Richardson's Chermical Engineering, 2002, vol. 2, fifth edition, pp. 612-629.

* cited by examiner

PROCESS FOR SEPARATING MONOCHLOROACETIC ACID AND DICHLOROACETIC ACID VIA EXTRACTIVE DISTILLATION

REFERENCE TO RELATED APPLICATIONS

This application is the U.S. National Phase of PCT/EP2012/054310 filed on Mar. 13, 2012, and claims the benefit of EP Application No. 11170773.3, filed on Jun. 21, 2011, and U.S. Application No. 61/504,422, filed on Jul. 5, 2011.

The present invention relates to a process for separating monochloroacetic acid and dichloroacetic acid from one another via extractive distillation.

The predominant industrial route for the production of monochloroacetic acid is by reacting acetic acid with chlorine. Such a process is commonly known and generally makes use of a reactor in which a mixture of liquid acetic acid (HAc) is reacted with chlorine under anhydrous conditions, in the presence of a catalyst. In the reactor, monochloroacetic acid (MCA) and gaseous HCl are formed together with by-products of which dichloroacetic acid (DCA) and trichloroacetic acid (TCA) are examples.

After chlorination, DCA is present in a significant amount in the MCA-containing reaction product mixture, typically about 3-10 wt %. To reduce the amount of DCA in the MCA, the MCA/DCA-containing product mixture should be subjected to a purification process. Known purification methods include (melt) crystallization and reduction of the DCA with hydrogen in the presence of a hydrogenation catalyst. These methods can be applied on MCA/DCA streams which have already been purified but still comprise a low amount of DCA, but also on streams which comprise a considerably higher amount of DCA (DCA concentrations typically in the range of between 50 ppm and 70 wt %).

With melt crystallization, the concentration of dichloroacetic acid in a crude monochloroacetic acid feed can only be reduced with a one-stage recrystallization by a factor of approximately 4, i.e., for example, from 3 to 0.7-0.8% by weight. Hence, for the production of pure monochloroacetic acid, the melt crystallization is repeated several times. After several crystallizations, a mother liquor remains comprising a mixture of monochloroacetic acid and dichloroacetic acid. Although this mother liquor still comprises at least 30% by weight of monochloroacetic acid, depending on the cooling conditions, it cannot be converted into a sellable product by further crystallization. Hence, there is a need for an economically feasible method for separating the monochloroacetic acid and the dichloroacetic acid from one another so that said mother liquor does not have to be discarded, and which may even make the melt crystallization process redundant.

As the boiling points of monochloroacetic acid and dichloroacetic acid are very close (189° and 194° C., respectively), they cannot easily be separated from one another by simple distillation because the volatility of the two components is nearly the same, causing them to evaporate at nearly the same temperature at a similar rate, making normal distillation impractical. However, it is known that components in a mixture having a relative volatility value close to 1 may be separated via extractive distillation. Extractive distillation is a distillation in the presence of a third component (hereinafter denoted as extractive agent or EA) which interacts differently with the components of the mixture, thereby causing their relative volatility to change. This enables the new three-part mixture to be separated by normal distillation. The essence of extractive distillation is for instance explained by J. F. Richardson, J. H. Harker, and J. R. Backhurst, in *Coulson and Richardson's Chemical Engineering*, Vol. 2, 5$^{th}$ edition (2002), Butterworth-Heinemann, pages 617-619, and by Hannsjörg Freund and Kai Sundmacher, in "Process Intensification, 4. Plant Level" (published Online: 15 Jul. 2011), page 22, in Ullman's Encyclopedia of Industrial Chemistry: *Extractive Distillation [187-190]*.

A method for separating monochloroacetic acid and dichloroacetic acid from each other by extractive distillation is known from JP 47-30165. It describes the use of sulfuric acid as extractant. Addition of sulfuric acid to a mixture comprising monochloroacetic acid and dichloroacetic acid results in an increased difference in volatilities. Upon distillation, dichloroacetic acid containing a small amount of monochloroacetic acid is distilled over the top, while the bottom product is a mixture of sulfuric acid and monochloroacetic acid containing a very small amount of dichloroacetic acid. The bottom product is subsequently distilled to yield monochloroacetic acid and sulfuric acid. A disadvantage of this method is, however, that the thus obtained monochloroacetic acid has to be subjected to a crystallization step for refining. Furthermore, traces of sulfuric acid that may end up in the DCA top product will lead to enhanced deactivation of the catalyst which is used in a subsequent hydrogenation step for conversion of DCA to MCA.

JP 47-29886 discloses a similar process wherein sulfolane is used as the extractive agent. It is true that the use of sulfolane as extractive agent has the advantage that the extractive agent can be recovered and reused relatively easily. However, also in this case, the degree of separation of monochloroacetic acid from dichloroacetic acid leaves room for improvement, since the achieved improvement in relative volatility of the MCA/DCA system is small.

It is therefore an object of the present invention to provide a process for separating monochloroacetic acid and dichloroacetic acid from one another via extractive distillation which is economically feasible because good separation is achieved, while at the same time the used extractive agent can be regenerated relatively easily.

It has surprisingly been found that this objective is met if a specific extractive agent is used.

More specifically, the present invention relates to a process for separating monochloroacetic acid and dichloroacetic acid from one another via extractive distillation, comprising the steps of (i) contacting a mixture comprising monochloroacetic acid and dichloroacetic acid with an extractive agent which is chemically stable and has a $BF_3$ affinity of between 65 kJ/mole and 110 kJ/mole, (ii) distilling the mixture to obtain a monochloroacetic acid stream and a stream comprising dichloroacetic acid and the extractive agent, and (iii) regenerating the extractive agent. It is noted that the mixture comprising monochloroacetic acid and dichloroacetic acid is contacted with the extractive agent prior to and/or during distillation step (ii). More particularly, in step (i), contacting the mixture comprising MCA and DCA with an extractive agent can take place inside the column which is used to perform the extractive distillation. However, it is also possible to contact the mixture comprising MCA and DCA with the extractive agent prior to their entrance into the column used for the extractive distillation (i.e. premixing the mixture comprising MCA and DCA with extractive agent and feeding the resulting mixture to the column in order to perform the extractive distillation). A combination of the two techniques is also possible. It is noted that it is preferred to contact the mixture comprising MCA and DCA with an extractive agent inside the extractive distillation column. In that case, preferably, the extractive agent is fed to said column at a stage above the stage at which the mixture comprising MCA and DCA is fed to said column, as in that case there will be an excess of extractive agent present higher up in the column to catch any traces of DCA.

The term "extractive agent" as used throughout this specification is meant to denote any additive which forms a stronger complex with dichloroacetic acid (DCA) than with monochloroacetic acid (MCA). By definition, the extractive agent is less volatile than the components to be separated.

The $BF_3$ affinity of an extractive agent can be determined according to the test method which is described in Christian Laurence and Jean-Francois Gal, *Lewis Basicity and Affinity Scales, Data and Measurement*, 2010, John Wiley & Sons Ltd, ISBN 978-0-470-74957-9, Chapters 3 and 7. A short description of said test method will be provided below.

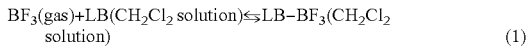

(with LB being Lewis Base, i.e. the extractive agent)

Heat evolved in complexation reaction (1) is measured in a heat-flux microcalorimeter thermoregulated at 298K. The measuring cell contains ~3 cm$^3$ of a dilute solution of Lewis base (i.e. extractive agent) in $CH_2Cl_2$. The base concentration depends on its strength: it usually ranges from 0.2 mole/L for strong bases to 1 mole/L for weak bases. Aliquots in the range (1-3) 10$^{-4}$ mole of gaseous $BF_3$ are added to the solution of base by means of a vacuum line. Each addition of a quantity of $BF_3$ (n mole) generates a quantity of heat, Q. When the reaction is complete, the enthalpy of complexation for each addition, $\Delta H°$, is defined as the Q/n ratio. The method is equivalent to a discontinuous titration of the base by the acid $BF_3$. One titration provides 6-8 $\Delta H°$ values. Their mean and the corresponding confidence limits, usually at the 95% level, are calculated. The precision is fairly good (0.2-0.5% within a set, 0.5-1% between sets) and the accuracy is estimated as 1-2%.

It is noted that it is essential to use dry solvents and reactants because traces of humidity (and also other impurities) tend to induce an additional heat of reaction. Moreover, boron trifluoride releases hydrogen fluoride by slow hydrolysis, resulting in etching of the glass parts of the system (see also Chapter 7.1.2 of the above-mentioned book of Laurence and Gal). It is furthermore noted that the calorimeter can be calibrated by the Joule effect (see Chapter 7.1.3 of the above-mentioned book of Laurence and Gal).

The extractive agent according to the present invention is chemically stable. To evaluate the stability of the extractive agent the following test can be conducted. Dichloroacetic acid and the extractive agent are added to a 10 mL vial in a 1:1 mole based ratio. The total amount of dichloroacetic acid and extractive agent mixture supplied to the vial is 2 mL. The vial containing the mixture is stored at a temperature of 160° C. for 24 hours. Subsequently, one droplet of the sample is added to 1.5 mL acetone. The mixture of the sample and the acetone is analyzed using GC-MS (Gas-chromatography-Mass Spectrometry) according to the following protocol:

Equipment: Shimadzu GC-17A Gas Chromatograph+Shimadzu GC MS-QP5000 Detector MS
Column: Chrompack VF-1 ms 25 m*0.25 mm ID DF=0.40 µm 100% dimethylpolysiloxane
GC method: Injection temperature: 300° C.
  Interface temperature: 250° C.
  Column inlet pressure: 24.5 kPa
  Column flow: 0.8 mL/min
  Linear velocity: 35.5 cm/sec
  Split ratio: 10
  Carrier: Helium
  Total flow: 9.4 mL/min
  Carrier flow: 9.4 mL/min
  Injection volume: 1 µL
  Start Temperature: 50° C.
  Heating rate: 10° C./min
  End temperature: 290° C. (9 minutes hold time)
MS settings: Start time: 1.4 min
  Stop time: 33 min
  Start m/z: 35 g/mole
  Stop m/z: 400 g/mole
  Scan speed: 2,000
  Interface temperature: 250° C.
  Acetone cut time: 1.4 min
  Detector voltage: 1.3 kV
  Threshold: 1,000
  Interval: 0.2 seconds The ratio of the peak area of the impurity over extractive agent should be below 0.3, preferably below 0.1, and more preferably below 0.05 to consider the extractive agent chemically stable.

These peak areas can be converted using conventional calibration techniques the skilled person is familiar with into percentages of degenerated extractive agent, based on the initial total amount of extractive agent used. Accordingly, the term "chemically stable" as used throughout the specification for the extractive agent denotes that less than 45% of extractive agent (relative on a mole basis) will be degenerated when kept for 24 hours at 160° C. in the presence of dichloroacetic acid in a 1:1 mole ratio. Preferably, it denotes that less than 15% of extractive agent (relative on a mole basis) will be degenerated when kept for 24 hours at 160° C. in the presence of dichloroacetic acid in a 1:1 mole ratio. Most preferably, it denotes that less than 7.5% of extractive agent (relative on a mole basis) will be degenerated when kept for 24 hours at 160° C. in the presence of dichloroacetic acid in a 1:1 mole ratio.

The extractive agent is preferably selected from the group consisting of phosphine oxides, aldehydes, ketones, ethers, and amides which are chemically stable and have a $BF_3$ affinity of between 65 kJ/mole and 110 kJ/mole. More preferably, the extractive agent is selected from the group consisting of aldehydes, ketones, ethers, and amides which are chemically stable and have a $BF_3$ affinity of between 65 kJ/mole and 110 kJ/mole. Most preferably, the extractive agent is selected from the group consisting of ketones and ethers which are chemically stable and have a $BF_3$ affinity of between 65 kJ/mole and 110 kJ/mole.

As said, the extractive agent according to the present invention has a $BF_3$ affinity of at least 65 kJ/mole. Preferably, however, it has a $BF_3$ affinity of at least 70 kJ/mole and most preferably of at least 75 kJ/mole.

The extractive agent according to the present invention has a $BF_3$ affinity of at most 110 kJ/mole. Preferably, however, it has a $BF_3$ affinity of at most 100 kJ/mole, and most preferably, it has a $BF_3$ affinity of at most 90 kJ/mole.

In a particularly preferred embodiment, the extractive agent is selected from the group consisting of tetraglyme, diethylene glycol dibutyl ether, dihexyl ether, diethylene glycol dipentyl ether, and dihexyl ketone.

As described above, in the process according to the present invention, a mixture comprising monochloroacetic acid and dichloroacetic acid is contacted with the extractive agent according to the present invention. Besides MCA and DCA it may furthermore comprise acetic acid. Said mixture preferably comprises at least 50 ppm of DCA, more preferably at least 500 ppm of DCA, and most preferably at least 5,000 ppm of DCA. Preferably, it comprises no more than 70 wt % of DCA, more preferably no more than 60 wt % of DCA, and most preferably no more than 50 wt % of DCA.

The extractive agent is preferably used in step (i) in such an amount that the ratio between extractive agent and DCA is at least 0.5, on a mole basis, more preferably at least 1.0, on a mole basis, and most preferably at least 2.5, on a mole basis. For the sake of clarity, by the ratio between extractive agent and DCA is meant the total amount of extractive agent fed to the distillation column over the total amount of DCA fed to the distillation column, both on a mole basis. The extractive agent is preferably used in such an amount that the ratio between extractive agent and DCA is at most 50, on a mole basis, more preferably at most 30, on a mole basis, even more preferably at most 20, on a mole basis, and most preferably at most 10, on a mole basis.

The mixture comprising MCA, DCA, and extractive agent is distilled to obtain a monochloroacetic acid stream on the one hand and on the other hand, a stream comprising dichloroacetic acid and the extractive agent. This extractive distillation step (step ii) is preferably performed at a pressure of below 500 mbar, more preferably below 250 mbar, and most preferably below 100 mbar.

The extractive distillation step is preferably performed with a temperature at the bottom of the distillation column of below 453 K, more preferably below 433 K, even more preferably below 413 K, and most preferably below 393 K. In a next step, the extractive agent is regenerated by stripping or, preferably, by distillation of the stream comprising dichloroacetic acid and extractive agent. This step furthermore yields dichloroacetic acid. Preferably, the regenerated extractive agent is recycled to step (i) of the process according to the present invention.

Step (iii) is preferably performed at a pressure of below 250 mbar, more preferably below 100 mbar, most preferably below 75 mbar.

In the case of a distillation step, the temperature at the bottom of the distillation column preferably is below 493 K, more preferably below 473 K, more preferably still below 453 K, and most preferably below 433 K.

A skilled person will understand that at identical pressures, the temperature at which the separation according to step (iii) of the present process is performed is higher than the temperature at which the extractive distillation of step (ii) is performed.

Suitable equipment which can be used to perform the extractive distillation step (step (ii)) according to the present invention includes conventional distillation columns comprising a reboiler and condenser. The regeneration step (step (iii)) can be performed in a conventional stripping column or a conventional distillation column, of which the latter is preferred.

In a preferred embodiment, at least part of the process according to the present invention is performed in a Petlyuk column or a divided wall column. Petlyuk columns and divided wall columns are conventionally known and for instance described by I. Dejanović, Lj. Matijašević, and Ž. Olujić in *Chemical Engineering and Processing* 49, 2010, pp. 559-580. The use of a Petlyuk or a divided wall column for carrying out the process of the present invention has the advantage that at least steps (ii) and (iii) of the present process are combined into one step. Most preferably, however, steps (i), (ii), and (iii) are combined into one single step or unit operation by using a Petlyuk or a divided wall column.

The process according to the present invention can be used for further purification of streams comprising MCA and DCA which have already been purified, e.g. via a crystallization process, but still comprise a low amount of DCA. It is also suitable for the purification of crude streams which comprise a considerably higher amount of DCA.

The DCA obtained via the process according to the present invention can subsequently be subjected to a hydrogenation step by contacting it with hydrogen in the presence of a hydrogenation catalyst (such as for example disclosed in EP 557169) to produce MCA.

The process according to the present invention is further illustrated by the following non-limiting examples.

EXAMPLE 1

This example demonstrates the limited effect of sulfolane in the extractive distillation of a monochloracetic acid (MCA)/dichloroacetic acid (DCA)-containing feed on the selectivity of the separation.

To determine the effect of sulfolane on the vapour-liquid equilibrium of the MCA/DCA mixture, an ebulliometer (Fischer VLE 602D) was used. In this ebulliometer the equilibrium vessel is a dynamic recirculating still, equipped with a Cottrel circulation pump. The heating capacity and the pressure were controlled using a control unit (Fischer system M101). The vapour condensation rate was kept constant at one drop per second. The condenser was operating at 70° C. The pressure was kept constant within a deviation of 0.02 kPa and the equilibrium temperature was measured with an uncertainty of 0.1° C. Equilibrium was reached after approximately 30-45 minutes, when the vapour temperature and the distillation rate were both constant. Samples of 30 μL from both the vapour and the liquid phase were taken with a 500 μL syringe. These samples were diluted with 0.75 mL of acetonitrile and 0.75 mL of water. The concentrations of the components were analyzed using high pressure liquid chromatography (HPLC, Varina Prostar). A silica-based Grace Prevail™ Organic Acid column (250 mm×4.6 mm) with a particle size of 5 μm was used. The temperature of the column was kept constant in an oven (Varian Prostar Model 510) at 313.2 K for all measurements. Detection of MCA and DCA was done using a UV detector (Varian Prostar Model 310) at 210 nm. The concentration of sulfolane was calculated by means of a mass balance over the sample. The eluent flow was 1 mL/min and consisted of acetonitrile (5 vol %) and an orthophosphoric acid solution (19 g/L) in Milli-Q water (95%). The column was regenerated after each injection with pure acetonitrile. Each sample was injected twice. The mole fractions of the components in both the vapour and the liquid phase were obtained within an accuracy of 0.001 in mole fraction.

MCA (≥99.0%) and DCA (≥99.0%) used in this example were obtained from Sigma-Aldrich. Sulfolane (≥98%) was obtained from Fluka. All chemicals were used without further purification.

Before the experiment a solution of about 100 mL was prepared, in which the MCA/DCA ratio was 4/1 on a mole basis. Two sulfolane/DCA ratios were utilized; 1/2 and 1/1, on a mole basis. All starting weights of the chemicals used for the vapour-liquid equilibrium experiments are shown in Table 1. The vapour-liquid equilibrium experiments were performed at 5, 7.5, and 10 kPa pressure. One experiment was performed on an extractive agent-free basis to measure the relative volatility for DCA and MCA without the presence of the extractive agent. Moreover, one experiment was performed for the benchmark extractive agent sulfolane. The relative volatility α presented in this example was calculated as follows:

$$\alpha = \alpha_{MCA/DCA} = (y_{MCA}/y_{DCA})/(x_{MCA}/x_{DCA})$$

where $y_{MCA}$ and $y_{DCA}$ are the weight fractions of MCA and DCA in the vapour phase, and $x_{MCA}$ and $x_{DCA}$ are the weight fractions of MCA and DCA in the liquid phase. The results of the vapour-liquid equilibrium experiments are listed in Table 2. The data in Table 2 clearly show that the addition of sulfolane results in a limited increase in the MCA/DCA relative volatility. It therefore has a slightly (but limited) positive effect on the separation of MCA and DCA during distillation. However, for practical applications, this effect is too small to obtain acceptable separation.

TABLE 1

| EA (=Extractive Agent) | EA/DCA [mole base] | Mass MCA [g] | Mass DCA [g] | Mass extractive agent [g] |
| --- | --- | --- | --- | --- |
| Sulfolane | 1/1 | 83.5 | 28.5 | 26.5 |
|  | 1/2 | 93.2 | 31.8 | 14.8 |
| EA free | — | 106.8 | 36.8 | — |

TABLE 2

| EA | BF$_3$ affinity [kJ/mole] | EA/DCA [mole base] | P = 5 kPa | | P = 7.5 kPa | | P = 10 kPa | |
| --- | --- | --- | --- | --- | --- | --- | --- | --- |
| | | | α [—] | T [K] | α [—] | T [K] | α [—] | T [K] |
| Sulfolane | 51 | 1/1 | 1.6 | 385.8 | 1.6 | 395.2 | 1.6 | 402.6 |
|  |  | 1/2 | 1.4 | 381.9 | 1.4 | 391.1 | 1.4 | 398.1 |
| EA free |  | — | 1.3 | 380.9 | 1.3 | 389.9 | 1.3 | 397.0 |

EXAMPLE 2

This example demonstrates the benefits of various extractive agents over sulfolane in the extractive distillation of a monochloracetic acid (MCA)/-dichloroacetic acid (DCA) feed. As discussed below, the experiments in this example have been performed with the same equipment, pressure conditions, and extractive agent/DCA mole ratios as used in Example 1.

To determine the effect of the several extractive agents on the vapour-liquid equilibrium of the MCA/DCA mixture, an ebulliometer (Fischer VLE 602D) was used. In this ebulliometer the equilibrium vessel is a dynamic recirculating still, equipped with a Cottrel circulation pump. The heating capacity and the pressure were controlled using a control unit (Fischer system M101). The vapour condensation rate was kept constant at one drop per second. The condenser was operating at 70° C. The pressure was kept constant within a deviation of 0.02 kPa and the equilibrium temperature was measured with an uncertainty of 0.1° C. Equilibrium was reached after approximately 30-45 minutes, when the vapour temperature and the distillation rate were both constant. Samples of 30 μL from both the vapour and the liquid phase were taken with a 500 μL syringe. For the experiments with the extractive agents tetraglyme, succinonitrile, tri-n-butylphosphate, tri-n-hexylamine, and diethylene glycol dibutyl ether, these samples were diluted with 0.75 mL of acetonitrile and 0.75 mL of water. The concentrations of the components were analyzed using high pressure liquid chromatography (HPLC, Varina Prostar). A silica-based Grace Prevail™ Organic Acid column (250 mm×4.6 mm) with a particle size of 5 μm was used. The temperature of the column was kept constant in an oven (Varian Prostar Model 510) at 313.2 K for all measurements. Detection of MCA and DCA was done using a UV detector (Varian Prostar Model 310) at 210 nm. The concentration of the extractive agent was calculated by means of a mass balance over the sample. The eluent flow was 1 mL/minute and consisted of 5 vol % acetonitrile and 95 vol % orthophosphoric acid solution (19 g/L) in Milli-Q water. The column was regenerated after each injection with pure acetonitrile. Each sample was injected twice. The mole fractions of the components in both the vapour and the liquid phase were obtained within an accuracy of 0.001 in mole fraction.

For the experiments with the extractive agent diethylene glycol dipentyl ether, dihexyl ketone, dihexyl ether and, tri-n-octylphosphine oxide, these samples were diluted with 1.5 mL of acetonitrile. The concentrations of the components were analyzed using high pressure liquid chromatography (HPLC, Varina Prostar). A silica-based Grace Prevail™ Organic Acid column (250 mm×4.6 mm) with a particle size of 5 μm was used. The temperature of the column was kept constant in an oven (Varian Prostar Model 510) at 313.2 K for all measurements. Detection of MCA and DCA was done using a UV detector (Varian Prostar Model 310) at 210 nm. The concentration of the extractive agent was calculated by means of a mass balance over the sample. The eluent flow was 1 mL/minute and consisted of 15 vol % acetonitrile and 85 vol % orthophosphoric acid solution (19 g/L) in Milli-Q water. The column was regenerated after each injection with pure acetonitrile. Each sample was injected twice. The mole fractions of the components in both the vapour and the liquid phase were obtained within an accuracy of 0.001 in mole fraction.

MCA (≥99.0%) and DCA (≥99.0%) used in this example were obtained from Sigma-Aldrich. Tetraglyme (≥98.0%), succinonitrile (≥97.0%), tri-n-butylphosphate (≥99%), and tri-n-octylphosphine oxide (≥97.0%) were obtained from Fluka, and tri-n-hexylamine (≥96%), diethylene glycol dibutyl ether (≥99.0%), dihexyl ether (≥97.0%), and dihexyl ketone (≥97.0%) were obtained from Aldrich. Diethylene glycol dipentyl ether (≥99.0%) was obtained from Syncom. All chemicals were used without further purification.

Before the experiment a solution of about 100 mL was prepared, in which the MCA/DCA ratio was 4/1 on a mole basis. Two EA/DCA ratios were utilized; 1/2 and 1/1, on a mole basis. All starting weights of the chemicals used for the vapour-liquid equilibrium experiments are shown in Table 3. The vapour-liquid equilibrium experiments were performed at 5, 7.5, and 10 kPa pressure. The relative volatility α presented in this example was calculated as follows:

$$\alpha = \alpha_{MCA/DCA} = (y_{MCA}/y_{DCA})/(x_{MCA}/x_{DCA})$$

where $y_{MCA}$ and $y_{DCA}$ are the weight fractions of MCA and DCA in the vapour phase, and $x_{MCA}$ and $x_{DCA}$ are the weight fractions of MCA and DCA in the liquid phase. The results of the vapour-liquid equilibrium experiments are listed in Table 4. The data in Table 4 clearly show that all extraction agents except one outperform sulfolane, since they result in a considerable increase in the relative volatility $\alpha_{MCA/DCA}$ as compared to sulfolane. More particularly, succinonitrile, having a BF$_3$ affinity (describing Lewis basicity) of 60 kJ/mole, shows an insufficient increase in relative volatility. Thus, suitable extractive agents for improving the separation of MCA and DCA by extractive distillation are extractive agents having a BF$_3$ affinity (describing Lewis basicity) in excess of 65 kJ/mole (preferably in excess of 70 kJ/mole), since these extractive agents show a relative volatility in excess of 1.8 and several even in excess of 2.0 at a EA/DCA mole ratio of 1/1. This is higher than the relative volatility obtained with sulfolane. It therefore demonstrates the benefits of the extractive agents according to the present invention over sulfolane in the extractive distillation of a monochloracetic acid (MCA)/ dichloroacetic acid (DCA) feed.

TABLE 3

| EA | EA/DCA [mole base] | Mass MCA [g] | Mass DCA [g] | Mass EA [g] |
|---|---|---|---|---|
| Succinonitrile | 1/1 | 86.0 | 29.3 | 18.2 |
|  | 1/2 | 94.8 | 32.3 | 10 |
| Tri-n-butylphosphate | 1/1 | 59.8 | 20.4 | 42.1 |
|  | 1/2 | 76.3 | 26 | 26.9 |
| Diethylene glycol dipentyl ether | 1/1 | 59.20 | 20.2 | 38.58 |
|  | 1/2 | 75.84 | 25.86 | 24.72 |
| Diethylene glycol dibutyl ether | 1/1 | 62.5 | 21.3 | 36.1 |
|  | 1/2 | 78.5 | 26.8 | 22.7 |
| Tetraglyme | 1/1 | 65.4 | 22.3 | 38.5 |
|  | 1/2 | 80.7 | 27.5 | 23.7 |
| Dihexyl ketone | 1/1 | 63.1 | 21.5 | 33.1 |
|  | 1/2 | 79.0 | 26.9 | 20.7 |
| Dihexyl ether | 1/1 | 63.7 | 21.7 | 31.4 |
|  | 1/2 | 80.0 | 27.3 | 19.6 |
| Tri-n-octylphosphine oxide | 1/1 | 47.4 | 16.1 | 46.1 |
|  | 1/2 | 65.4 | 21.7 | 30.8 |
| Tri-n-hexylamine | 1/1 | 54.3 | 18.5 | 38.7 |
|  | 1/2 | 71.7 | 24.4 | 25.6 |

TABLE 4

| EA | $BF_3$ affinity [kJ/mole] | EA/DCA [mole base] | P = 5 kPa | | P = 7.5 kPa | | P = 10 kPa | |
|---|---|---|---|---|---|---|---|---|
|  |  |  | α [—] | T [K] | α [—] | T [K] | α [—] | T [K] |
| Succinonitrile | 60 | 1/1 | 1.4 | 385.6 | 1.4 | 396.2 | 1.4 | 403.8 |
|  |  | 1/2 | 1.3 | 382.2 | 1.3 | 392.2 | 1.3 | 400.1 |
| Tri-n-butylphosphate | 85 | 1/1 | 2.2 | 386.0 | 2.2 | 395.5 | 2.2 | 402.9 |
|  |  | 1/2 | 1.8 | 382.2 | 1.7 | 391.5 | 1.7 | 398.5 |
| Diethylene glycol dipentyl ether | 79 | 1/1 | 2.3 | 388.8 | 2.2 | 398.1 | 2.1 | 405.0 |
|  |  | 1/2 | 1.8 | 384.8 | 1.8 | 394.0 | 1.7 | 400.8 |
| Diethylene glycol dibutyl ether | 79 | 1/1 | 2.3 | 387.4 | 2.2 | 396.6 | 2.2 | 403.6 |
|  |  | 1/2 | 1.8 | 383.6 | 1.8 | 392.8 | 1.7 | 399.8 |
| Tetraglyme | 84 | 1/1 | 2.4 | 391.6 | 2.3 | 400.9 | 2.3 | 408.1 |
|  |  | 1/2 | 1.9 | 385.3 | 1.9 | 394.4 | 1.8 | 401.6 |
| Dihexyl ketone | 73 | 1/1 | 1.8 | 391.3 | 1.8 | 397.6 | 1.8 | 403.2 |
|  |  | 1/2 | 1.6 | 388.4 | 1.6 | 395.4 | 1.6 | 401.2 |
| Dihexyl ether | 84 | 1/1 | 2.0 | 389.4 | 2.0 | 396.0 | 2.0 | 400.9 |
|  |  | 1/2 | 1.6 | 386.9 | 1.6 | 393.6 | 1.6 | 399.4 |
| Tri-n-octylphosphine oxide | 120 | 1/1 | 2.8 | 385.8 | 2.7 | 395.2 | 2.6 | 402.6 |
|  |  | 1/2 | 2.0 | 381.8 | 1.9 | 391.1 | 1.9 | 398.1 |
| Tri-n-hexylamine | 135 | 1/1 | 4.7 | 391.7 | 4.5 | 401.6 | 4.1 | 409.6 |
|  |  | 1/2 | 2.6 | 383.2 | 2.5 | 393.1 | 2.4 | 400.3 |

EXAMPLE 3

To validate whether the extractive agents from Example 2 can be regenerated, vapour-liquid equilibrium experiments have been performed for the extractive agents in the presence of DCA. These regeneration experiments were performed with the same equipment, pressure conditions, analytical method, and extractive agents as in Example 2

Before the experiment a solution of 100 mL was prepared in which the EA/DCA mole ratio was 1/1. This is the expected composition from the extractive distillation column. For some of the extractive agents for which the regeneration was successful for the EA/DCA mole ratio of 1/1, regeneration experiments for the EA/DCA mole ratios of 5/1 and 9/1 have been performed as well. These high EA/DCA compositions are expected in the bottom of the regeneration column. All starting weights of the regeneration experiments are shown in Table 5.

The relative volatility α presented in this example was calculated as follows:

$$\alpha = \alpha_{DCA/EA} = (y_{DCA}/y_{EA})/(x_{DCA}/x_{EA})$$

where in this example $y_{DCA}$ and $y_{EA}$ are the weight fractions of DCA and EA in the vapour phase, and $x_{DCA}$ and $x_{EA}$ are the weight fractions of DCA and EA in the liquid phase.

The results of the vapour-liquid equilibrium experiments are listed in Table 6. Table 6 shows that the long chain ethers diethylene glycol dibutyl ether, diethylene glycol dipentyl ether, and tetraglyme can be regenerated. The same applies for dihexyl ether and dihexyl ketone. For tri-n-hexylamine, succinonitrile, tri-n-octylphosphine oxide, and tri-n-butylphosphate, the regeneration experiments were unsuccessful. For the extractive agents tri-n-hexylamine and tri-n-octylphosphine oxide, the complex formed with DCA was too strong and no vapour phase was formed in the ebulliometer (meaning that the extractive agent and DCA cannot be separated). Succinonitrile and tri-n-butylphosphate were both unstable in the strong acid environment (measured according to stability test mentioned in the description) and consequently did not fulfil the chemical stability criterion for suitable extractive agents. This example shows that stability of the extractive agents in a strong acid environment is a prerequisite for the suitability of the extractive agent for this process. Furthermore, it shows that for proper regeneration of the extractive agents, extractive agents with a $BF_3$ affinity (describing Lewis basicity) below 110 kJ/mole are needed, since these extractive agents show a relative volatility in excess of 2.0 during regeneration at an extractive agent/DCA mole ratio of 1/1. For the extractive agents with a $BF_3$ affinity between 65 k/mole and 110 kJ/mole, and preferably between 70 kJ/mole and 100 kJ/mole, good separation is obtained in both the extractive distillation (see Table 4 in Example 2) and in the regeneration (see Table 6 in this example).

TABLE 5

| EA | EA/DCA [mole ratio] | Mass DCA [g] | Mass EA [g] |
|---|---|---|---|
| Diethylene glycol dipentyl ether | 1/1 | 35.6 | 67.9 |
|  | 9/1 | 5.0 | 85.1 |
| Diethylene glycol dibutyl ether | 1/1 | 65.3 | 38.2 |
|  | 5/1 | 9.2 | 91.3 |
|  | 9/1 | 5.8 | 83.7 |
| Tetraglyme | 1/1 | 40.9 | 72.3 |
|  | 5/1 | 35.0 | 102 |
|  | 9/1 | 6.1 | 95.9 |
| Dihexyl ketone | 1/1 | 50.1 | 77.1 |
|  | 9/1 | 5.75 | 79.5 |
| Dihexyl ether | 1/1 | 40.6 | 58.7 |
|  | 9/1 | 5.87 | 76.3 |
| Succinonitrile | 1/1 | 76.8 | 48.7 |
| Tri-n-butylphosphate | 1/1 | 74.3 | 35.4 |
| Tri-n-octylphosphine oxide | 1/1 | 70.3 | 23.8 |
| Tri-n-hexylamine | 1/1 | 64.5 | 30.3 |

TABLE 6

| EA | BF₃ affinity [kJ/mole] | EA/DCA [mole ratio] | P = 5 kPa α [—] | P = 5 kPa T [K] | P = 7.5 kPa α [—] | P = 7.5 kPa T [K] | P = 10 kPa α [—] | P = 10 kPa T [K] |
|---|---|---|---|---|---|---|---|---|
| Tri-n-hexylamine | 135 | 1/1 | No vapor phase obtained, recovery EA not possible | | | | | |
| Tri-n-octyl-phosphine oxide | 120 | 1/1 | No vapor phase obtained, recovery EA not possible | | | | | |
| Diethylene glycol dipentyl ether | 79 | 1/1 | 10.9 | 428.2 | 10.3 | 438.4 | 11.5 | 445.8 |
| | | 9/1 | 2.4 | 448.3 | 2.6 | 459.1 | 2.7 | 467.2 |
| Diethylene glycol dibutyl ether | 79 | 1/1 | 2.4 | 422.5 | 2.4 | 432.3 | 2.0 | 439.5 |
| | | 5/1 | 0.80 | 427.9 | 0.84 | 438.1 | 0.90 | 445.7 |
| | | 9/1 | 0.71 | 429.2 | 0.76 | 439.5 | 0.81 | 447.0 |
| Tetraglyme | 84 | 1/1 | 2.3 | 443.4 | 2.2 | 452 | 2.0 | 458.3 |
| | | 5/1 | 0.76 | 446.7 | 0.80 | 457.2 | 0.84 | 464.7 |
| | | 9/1 | 0.68 | 448.6 | 0.70 | 458.7 | 0.73 | 466.1 |
| Dihexyl ketone | 73 | 1/1 | 14.8 | 411.1 | 12.4 | 420.2 | 11.1 | 427.0 |
| | | 9/1 | 2.6 | 431.0 | 2.7 | 441.4 | 2.6 | 448.8 |
| Dihexyl ether | 84 | 1/1 | 2.1 | 401.0 | 2.3 | 409.8 | 2.3 | 416.4 |
| | | 9/1 | 0.85 | 403.3 | 0.94 | 413.1 | 1.0 | 420.3 |

The invention claimed is:

1. A process for separating monochloroacetic acid and dichloroacetic acid from one another via extractive distillation, comprising the steps of
  (i) contacting a mixture comprising monochloroacetic acid and dichloroacetic acid with an extractive agent which is chemically stable and which has a BF₃ affinity of between 65 kJ/mole and 110 kJ/mole, wherein the extractive agent is less volatile than the monochloroacetic acid and the dichloroacetic acid,
  (ii) distilling the mixture to obtain a monochloroacetic acid stream and a stream comprising dichloroacetic acid and the extractive agent, and
  (iii) regenerating the extractive agent.

2. The process according to claim 1, wherein the extractive agent is selected from the group consisting of phosphine oxides, aldehydes, ketones, ethers, and amides.

3. The process according to claim 1, wherein the extractive agent has a BF₃ affinity of between 75 kJ/mole and 90 kJ/mole.

4. The process according to claim 1, wherein dichloroacetic acid is present in the mixture comprising monochloroacetic acid and dichloroacetic acid in an amount of at least 50 ppm, and wherein the mixture further comprises acetic acid.

5. The process according to claim 1, wherein the mixture comprising monochloroacetic acid and dichloroacetic acid is contacted with the extractive agent at least one of prior to and during step (ii).

6. The process according to claim 1, wherein the extractive agent is selected from the group consisting of tetraglyme, diethylene glycol dibutyl ether, dihexyl ether, diethylene glycol dipentyl ether, and dihexyl ketone.

7. The process according to claim 1, wherein regenerated extractive agent is recycled to step (i).

8. The process according to claim 1, wherein step (ii) is carried out in a distillation column, comprising a reboiler and a condenser.

9. The process according to claim 8, wherein step (ii) is carried out at a pressure below 500 mbar and with a temperature at the bottom of said distillation column of below 453 K.

10. The process according to claim 1, wherein in step (iii) the extractive agent is regenerated by stripping or distillation of the stream comprising dichloroacetic acid and the extractive agent.

11. The process according to claim 10, wherein recovered dichloroacetic acid is subsequently subjected to a hydrogenation step to produce MCA.

12. The process according to claim 8, wherein step (iii) is carried out in a distillation column at a pressure below 250 mbar and with a temperature at the bottom of said distillation column of below 493 K.

13. The process according to claim 1, wherein the ratio between the extractive agent and dichloroacetic acid in step (i) is between 0.5 and 50, on a mole basis.

14. The process according to claim 1, wherein at least steps (ii) and (iii) are carried out in a Petlyuk column or a divided wall column.

15. The process according to claim 1, wherein dichloroacetic acid is present in the mixture comprising monochloroacetic acid and dichloroacetic acid in an amount of at least 500 ppm, and wherein the mixture further comprises acetic acid.

16. The process according to claim 2, wherein the extractive agent is selected from the group consisting of tetraglyme, diethylene glycol dibutyl ether, dihexyl ether, diethylene glycol dipentyl ether, and dihexyl ketone.

17. The process according to claim 4, wherein regenerated extractive agent is recycled to step (i).

18. The process according to claim 10, wherein step (iii) is carried out in a distillation column at a pressure below 250 mbar and with a temperature at the bottom of said distillation column of below 493 K.

19. The process according to claim 6, wherein the ratio between the extractive agent and dichloroacetic acid in step (i) is between 0.5 and 50, on a mole basis.

20. The process according to claim 13, wherein at least steps (ii) and (iii) are carried out in a Petlyuk column or a divided wall column.

* * * * *